United States Patent [19]

Losa Dominguez et al.

[11] Patent Number: 5,355,886
[45] Date of Patent: Oct. 18, 1994

[54] PROPHYLACTIC PROTECTOR FOR ECHOGRAPHIC PROBES

[76] Inventors: José F. Losa Dominguez; Jordi Briones Escubos; Xavier Julve Diaz; Francesc Prats Llopts, all of Paseo Bonanova, 44 bajos, E-08017 Barcelona, Spain

[21] Appl. No.: 98,326
[22] PCT Filed: Dec. 9, 1992
[86] PCT No.: PCT/ES92/00080
§ 371 Date: Aug. 5, 1993
§ 102(e) Date: Aug. 5, 1993
[87] PCT Pub. No.: WO93/11697
PCT Pub. Date: Jun. 24, 1993

[30] Foreign Application Priority Data

Dec. 10, 1991 [ES] Spain ............................ 9102748

[51] Int. Cl.⁵ .................................................. A61B 8/00
[52] U.S. Cl. ............................ 128/660.01; 128/662.06
[58] Field of Search .................... 128/660.01, 662.03, 128/662.05–662.06, 736

[56] References Cited

U.S. PATENT DOCUMENTS

| 4,593,699 | 6/1986 | Poncy et al. ................. 128/662.03 |
| 5,076,279 | 12/1991 | Arenson et al. ............ 128/662.03 X |
| 5,259,383 | 11/1993 | Holstein et al. ............ 128/662.03 X |

Primary Examiner—Francis Jaworski
Attorney, Agent, or Firm—Dennison, Meserole, Pollack & Scheiner

[57] ABSTRACT

Prophylactic protector for echographic probes comprised of two parts permanently joined by two points of permanent union of two diverging ears each joined by welding to a different lip of the loading mouth of the external envelope, which wings, without touching them, are separated and open the mouth while following the separation motion of the lips, with which they are integral, of the loading mouth of the opaque, flexible external envelope, thereby allowing to introduce the echoprobe. In the mouth of the elastic sheath there is arranged a continuous throat, wherein is pressure-fitted a rigid linking ring to the annular groove of the echoprobe handle.

2 Claims, 1 Drawing Sheet

PROPHYLACTIC PROTECTOR FOR ECHOGRAPHIC PROBES

BACKGROUND OF THE INVENTION

Field of the Invention

The object of the present invention is a prophylactic protector to be assembled, for echographic probes.

Hitherto echographic probes have been protected by means of isolated prophylactics (preservatives) in common usage. The latter have been used owing to their considerable elasticity, although they are not perfectly adapted to the form of the echographic probe. The object of their use is to prevent direct contact between the body of the echographic probe and that of the patients. The echographic probe is introduced into these isolated prophylactics.

Additionally, known prophylactics have a lubricating gel spread over their entire surface, both internally and externally. This fluid permits perfect contact between the surface of the echographic probe and the inner wall of the prophylactic, as well as correct slippage of the resilient case and the echographic probe inserted therein, relative to the skin of the patient who is being examined. The fluid introduced prevents the presence of air bubbles between the various surfaces which are in contact, forming a perfect bridge for the ultrasonic waves emitted and received by the echographic probe, thus preventing distortions of the signal.

Known echographic probes are generally used for observing the development of the fetus throughout its gestation in the first three months and monitoring its development, or for other types of endopelvic analysis in both sexes, such that when the accessories in common and current usage for these prophylactics are seen, this is sometimes a shock for the patient being examined.

SUMMARY OF THE INVENTION

The new prophylactic protector to be assembled consists of two separate parts permanently connected to one another to form a single body until the moment of use, permitting one of the two parts, the resilient case, to be maintained constantly extended and accommodated inside an envelope of similar, superimposed, opaque sheets, and its edges to be connected by thermal embossing, apart from the intake and outlet mouth of the outer laminate envelope, in which the embossing is cold in order to permit easy opening by separation of the lips of the mouth of the aforementioned outer envelope.

In order to connect the resilient part disposed along the inside of the envelope of the two opaque sheets which are connected by their edges, in the loading mouth inside the said resilient case there is disposed a pair of integral, resilient, diverging wings, which are permanently connected to the inner surfaces of the respective lips of the loading mouth of the outer case of resilient, opaque sheets, the latter being connected by their edges.

The permanent connection of the two separate parts disposed one inside the other, and connected to one another, which form the protector to be assembled, is permanent until the moment when the doctor has to inspect the human cavity by means of the echographic probe introduced into the protective body to be assembled.

At this moment the doctor introduces the journal of the grasping handle of the echographic probe, and connects it to the latter in a known manner.

By this means the doctor has the echographic probe disposed inside the resilient case, which is not visible from the exterior, since the latter is in turn introduced inside the outer envelope made of opaque, resilient material.

Thus, although the patient is watching the movement of the assembly into which the echographic probe is introduced, he does not obtain any impression of rejection by seeing the resilient case, since the latter is not visible externally as it is covered by the opaque material of the general envelope.

By this means the doctor can move from one side to another of the examination room, with the assembly of the echographic probe, the resilient case and the opaque outer envelope, without having to worry about concealing the presence of the resilient case, since, as already indicated, the latter cannot be seen from the outside.

Subsequently, when the patient is positioned in the examination chair, and his field of vision does not extend to the doctor who is at a distance from him, the latter separates the opaque covering envelope at will. For this purpose, continuing to hold the grasping handle of the echographic probe, with his other hand the doctor holds down the opaque outer envelope, and gives a quarter turn to the handle, relative to the opaque envelope held down with his other hand, the opaque envelope not being turned, thus giving rise to detachment of the points of connection by thermal welding of the wings, to the inner surface of the lips of the mouth of the opaque envelope, which by this means is separated from the resilient case which holds the echographic probe connected to the grasping handle. When the general opaque envelope is pulled, this lays bare the inner resilient case which contains the echographic probe, which thus, at that moment, is ready to be introduced into the human cavity concerned, without having been seen bare by the patient, and without the resilient case itself or the echographic probe introduced therein having been handled.

Additionally, the resilient case which contains the echographic probe is provided in its mouth with a neck, in the inner wall of which there is provided an annular throat into which there is pressure fitted a rigid ring which is thus anchored therein, the purpose of the rigid ring being to provide the connection with the throat disposed outside the journal of the grasping handle, when, before separating the connection of the resilient case to the intake and outlet mouth of the general, opaque, resilient sheet envelope, this journal is pressure fitted inside the throat of the mouth of the resilient case, and the rigid ring of the latter is pressure fitted in the outer annular throat of the journal of the grasping handle, thus maintaining the resilient case connected rigidly to the end of the grasping handle.

It can thus be seen that also during the operations of fitting the grasping handle to the echographic probe, and during introduction of the latter into the case, there is no contact between the doctor's fingers, and the walls of the echographic probe or those of the case.

The prophylactic protector to be assembled, for echographic probes, is vacuum packed in order to prevent the material from being damaged by the oxygen in the air, and additionally in order to prevent the lubricating gel from being lost from its surface.

In order to illustrate the above-described, the present description is accompanied by a page of drawings, which forms an integral part thereof, showing in a simplified manner and schematically an embodiment, purely by way of illustration, and without limiting the practical possibilities of the invention.

BRIEF DESCRIPTION OF THE DRAWINGS

In these drawings.

DESCRIPTION OF THE INVENTION

Figure 1:
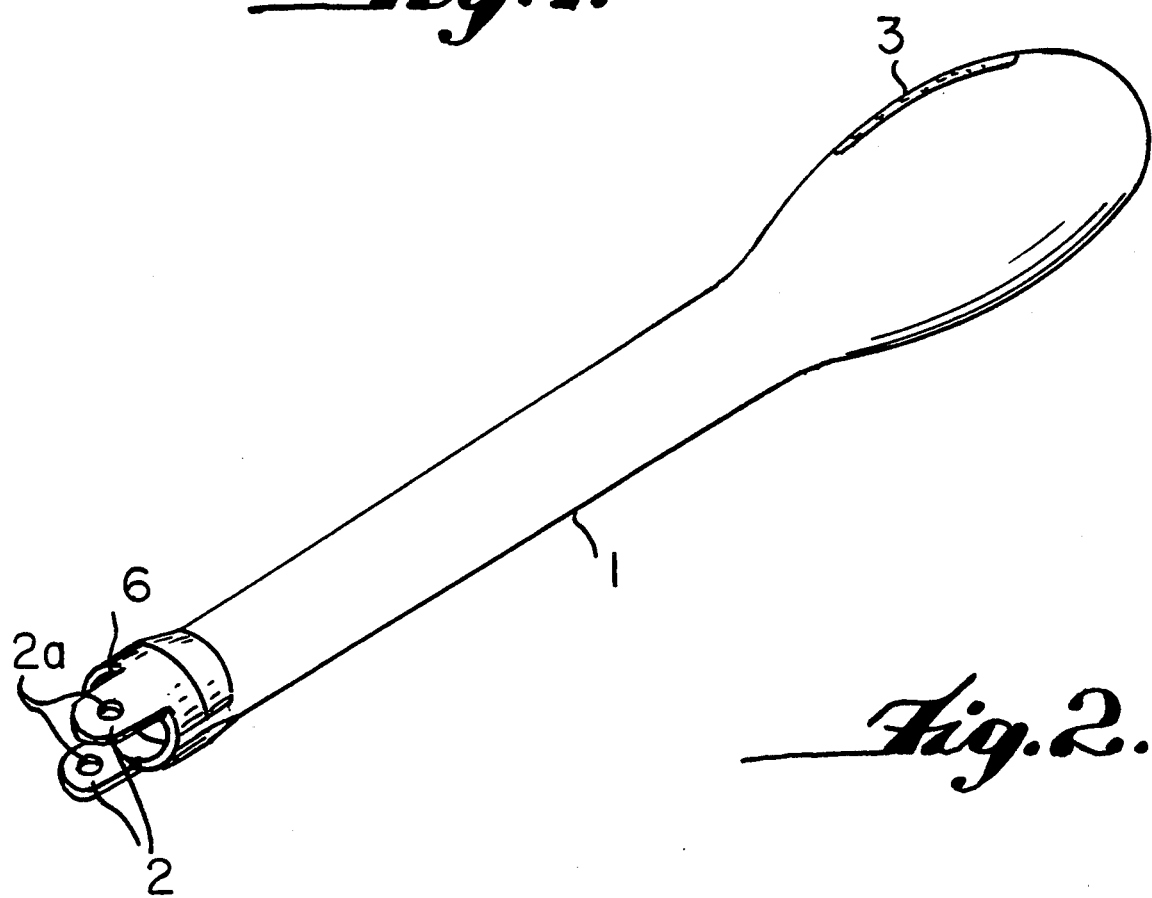
FIG. 1 shows only the resilient case of the prophylactic protector to be assembled, for echographic probes.
Figure 2:
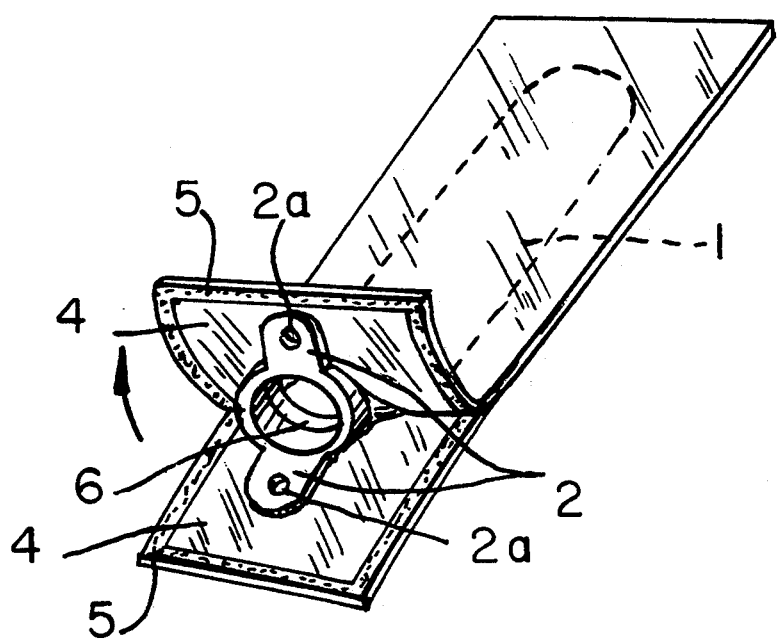
FIG. 2 shows the new protector ready assembled, forming a single inseparable assembly in its open envelope, before being used.

According to the drawings and their numbering, the prophylactic protector to be assembled, for echographic probes, comprises substantially two parts which form a single body, one part 1 being in the form of an internal case made of resilient material (preferably latex), of which the form coincides with the standard form of echographic probes. In the open end of the resilient case 1, the latter comprises a pair of wings 2 which are used in order to connect permanently the ends thereof, by means of two points of welding to the inner surface of the respective lip of the loading mouth of the outer envelope made of opaque resilient sheets, in the inside of which the inner resilient case which protects the echographic probe is introduced, extended and connected permanently by means of the above-described connection points.

The outer envelope is of the type which consists of two similar sheets of resilient, opaque material, the inner surface of which is provided with a layer of thermofusible material which enables the edges of the two superimposed opaque sheets to be connected to one another by means of thermal embossing, except in the area of loading of the opaque outer envelope, and the lips thereof are connected only by cold embossing, in order to facilitate opening by separation of the lips of the said mouth.

Since the wings of the mouth of the inner resilient case are connected integrally and permanently to the inner walls of the lips of the mouth of the opaque, flexible, laminate envelope, by two thermal welding points, the remainder of the entire body of the resilient case accommodated inside the opaque outer envelope is introduced and extended without being connected to the said outer envelope.

Thus when the opaque, resilient, outer envelope is opened by separating the connection of its lips, the mouth which is integral with the inner resilient case opens automatically, without touching the case, by stretching in opposite directions of its wings, which are connected by two welding points to the lips of the general opaque envelope, following the separation movement of these lips. Thus, the mouth of the resilient case opens automatically, without needing to be touched.

This automatic opening permits introduction of the echographic probe which is temporarily connected to the grasping handle thereof. By this means, the lubricating gel provided on the surface of the resilient case of the echographic probe is likewise untouched, and is therefore not removed from the outer surface of the resilient case, thus remaining aseptic during the positioning process.

In order to anchor the throat of the mouth of the resilient case to the end of the grasping handle which supports the echographic probe, when the latter has been introduced, and in order to maintain it firm and taut owing to the distension produced by the body of the echographic probe introduced, during the time when the analysis is being carried out, an inner ring 6 is pressure fitted without interruption in an annular groove provided in the inner part of the neck of the mouth in which the wings of connection of the inner resilient case to the opaque outer envelope meet, which rigid ring is pressure fitted in another, likewise continuous annular groove, adjacent the end of the grasping handle of the echographic probe.

As is conventional, the inner resilient part 1 has known lubricating gel 3 applied to its inner and outer surfaces, thus permitting regular contact between the various surfaces and preventing the formation of air bubbles, such that the ultrasonic waves pass through the protector without interference.

The protective resilient case extended inside the general outer envelope is vacuum packed between the two thermally welded sheets 4, such that in order to open it, the sheets must be separated from one another, thus simultaneously opening the mouth of the inner resilient case, for which purpose a non-thermally welded strip 5, suitable for starting the opening of the envelope, is provided. If the sheets are opened to a specific point, this reveals the wings, which are partially integral with both sheets, by means of two thermal rivets 2a, such that simply opening the envelope facilitates opening of the protector consisting of the resilient inner case, which is ready to accommodate the echographic probe, all without having to be handled directly by the doctor.

Finally, it must be emphasised that the prophylactic protector is disposable, i.e. it is only used once, thus making it even more hygienic. It is understood that in the present case, the details of form and construction may vary, provided that they do not substantially alter, change or modify the invention.

We claim:

1. Prophylactic protector for echographic probes, comprising:

an inner, isolated resilient case, an outer isolated envelope for receiving said inner isolated resilient case, said outer envelope consisting of two superimposed resilient opaque sheets and a loading mouth, wherein a surface of each of said sheets having a thermofusible layer, and edges connected by thermal embossing, the loading mouth having a pair of lips connected only by cold embossing, wherein the assembled prophylactic protector includes the outer envelope and the inner case forming a single body, the inner case being extended inside the outer envelope and connected by means of two permanent connection points, until moment of use, to the inner surface of the lips of the loading mouth of the outer envelope, and at least two wings, for providing the two permanent connection points, integral with two opposite points of the edge of the mouth of the inner case, and connected by these points to the inner surface of the lips of the mouth of the outer envelope, said at least two wings, being integral with the inner surface of the respective lips of the loading mouth of the envelope, following the movement of opening by separation of said lips, and for pulling at the two opposite points of the mouth of the case wherein the mouth opens automatically.

2. Prophylactic protector for echographic probes according to claim 1, in which the mouth of the inner case has a continuous throat, and inside said continuous throat is an annular groove for pressure fitting a rigid ring, and said rigid ring connected to the outer annular groove of the end of the grasping handle of the echographic probe.

* * * * *